(12) United States Patent
Blodgett et al.

(10) Patent No.: US 10,413,186 B2
(45) Date of Patent: Sep. 17, 2019

(54) COHERENT OPTICAL IMAGING FOR DETECTING NEURAL SIGNATURES AND MEDICAL IMAGING APPLICATIONS USING HOLOGRAPHIC IMAGING TECHNIQUES

(71) Applicant: The Johns Hopkins University, Baltimore, MD (US)

(72) Inventors: David W. Blodgett, Ellicott City, MD (US); Mark A. Chevillet, Silver Spring, MD (US); Michael P. McLoughlin, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 253 days.

(21) Appl. No.: 15/348,397

(22) Filed: Nov. 10, 2016

(65) Prior Publication Data
US 2017/0135583 A1    May 18, 2017

Related U.S. Application Data

(60) Provisional application No. 62/254,315, filed on Nov. 12, 2015.

(51) Int. Cl.
*A61B 5/00* (2006.01)
*G01B 9/02* (2006.01)
(Continued)

(52) U.S. Cl.
CPC .......... *A61B 5/0066* (2013.01); *A61B 5/0042* (2013.01); *A61B 5/0073* (2013.01); *A61B 5/0082* (2013.01); *A61B 5/4064* (2013.01); *G01B 9/0203* (2013.01); *G01B 9/02011* (2013.01); *G01B 9/02091* (2013.01); *G03H 1/0005* (2013.01); *G03H 1/0402* (2013.01); *G03H 1/0443* (2013.01); *G03H 1/0465* (2013.01); *G03H 1/265* (2013.01); *A61B 2576/026* (2013.01); *G02B 5/3025* (2013.01); *G02B 27/10* (2013.01); *G02F 2/00* (2013.01); *G03H 2001/0033* (2013.01); *G03H 2001/0436* (2013.01); *G03H 2001/0452* (2013.01); *G03H 2001/0469* (2013.01); *G03H 2222/20* (2013.01);
(Continued)

(58) Field of Classification Search
CPC combination set(s) only.
See application file for complete search history.

(56) References Cited

U.S. PATENT DOCUMENTS 5,568,315 A * 10/1996 Shuman ............... G02B 27/143
250/201.5
7,355,716 B2 * 4/2008 de Boer ............... A61B 5/0059
356/479

(Continued)

*Primary Examiner* — Janese Duley
(74) *Attorney, Agent, or Firm* — Sung T. Kim

(57) ABSTRACT

A neural imaging system may include an imaging array, an image data processor operably coupled to the imaging array to process image data received from the imaging array, and a beam angle separator disposed between the imaging array and an object being imaged. The beam angle separator may be configured to separate an object beam reflected from the object being imaged into a plurality of reference beams each having different angular separation with respect to the object beam. The image data processor may be configured to generate image data of the object for each one of the reference beams to correspond to a respective different depth within the object.

20 Claims, 5 Drawing Sheets

(51) Int. Cl.
  *G03H 1/00* (2006.01)
  *G03H 1/04* (2006.01)
  *G03H 1/26* (2006.01)
  *G02B 27/10* (2006.01)
  *G02B 5/30* (2006.01)
  *G02F 2/00* (2006.01)

(52) U.S. Cl.
  CPC ..... *G03H 2226/02* (2013.01); *G03H 2226/13* (2013.01)

(56) References Cited

U.S. PATENT DOCUMENTS

| | | | |
|---|---|---|---|
| 9,970,955 B1* | 5/2018 | Homyk | G01P 5/26 |
| 2008/0170204 A1* | 7/2008 | Podoleanu | A61B 3/102 |
| | | | 351/206 |
| 2011/0176190 A1* | 7/2011 | Golan | G03H 1/08 |
| | | | 359/9 |

* cited by examiner

COHERENT OPTICAL IMAGING FOR DETECTING NEURAL SIGNATURES AND MEDICAL IMAGING APPLICATIONS USING HOLOGRAPHIC IMAGING TECHNIQUES

CROSS-REFERENCE TO RELATED APPLICATIONS

This application claims the benefit of U.S. Provisional Application No. 62/254,315 filed on Nov. 12, 2015, the entire contents of which are hereby incorporated herein by reference.

TECHNICAL FIELD

Exemplary embodiments of the present disclosure generally relate to holographic imaging techniques, and more specifically relate to holographic imaging in connection with coherent optical imaging to detect neural signatures and to enable other medical imaging applications.

BACKGROUND

Imaging systems are employed for many different purposes. However, conventional imaging systems for imaging the brain or other parts of the body tend to be large and bulky and, thus, not easily portable. Conventional imaging systems may also require a lot of power for operation. Due to the size and complexity of conventional imaging systems, these systems tend to be expensive to procure, operate, and maintain.

BRIEF SUMMARY OF SOME EXAMPLES

In one example embodiment, a neural imaging system is provided. The neural imaging system may include an imaging array, an image data processor operably coupled to the imaging array to process image data received from the imaging array, and a beam angle separator disposed between the imaging array and an object being imaged. The beam angle separator may be configured to separate an object beam reflected from the object being imaged into a plurality of reference beams each having different angular separation with respect to the object beam. An image data processor may generate image data of the object for each of the reference beams, the image data for each of the reference beams corresponding to a different depth within the object.

In another example embodiment, a method of detecting neural signatures is provided. The method may include receiving an object beam reflected from an object, separating the object beam into a plurality of reference beams each having different angular separation with respect to the object beam, generating image data of the object for each of the reference beams corresponding to a different depth within the object, and transmitting the image data to an image data processor.

In another example embodiment, a brain computer interface sensor is provided. The brain computer interface sensor may include an imaging array configured to be operably coupled to an image data processor to process image data received from the imaging array, and a beam angle separator disposed between the imaging array and neural tissue being imaged. The beam angle separator is configured to separate an object beam reflected from the neural tissue being imaged into a plurality of reference beams each having different angular separation with respect to the object beam.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1A:
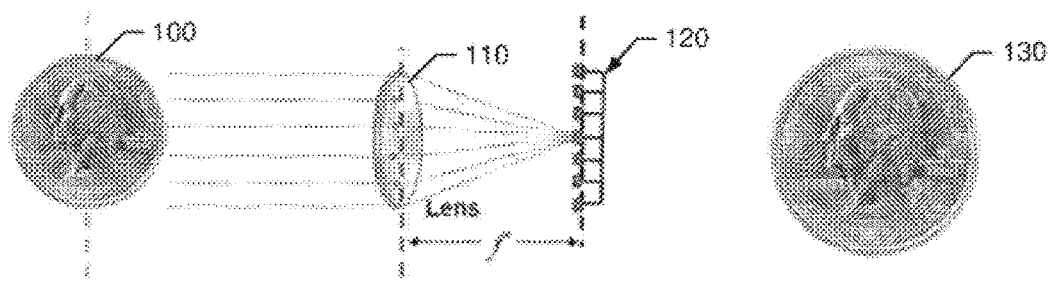
FIG. 1A illustrates a conceptual diagram showing one example of a conventional imaging system.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As used herein, the terms "component," "module," and the like are intended to include a computer-related entity, such as but not limited to hardware, firmware, or a combination of hardware and software. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/ module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

Holographic imaging is an approach that can be thought of as a lens-less imaging modality. In conventional imaging, ambient light scattered off of an object is collected by a lens and then imaged onto an array. The focal length of the lens system dictates the distance at which the objects are brought into focus. Conversely, in holographic imaging, the object is actively illuminated by a coherent light source, and the scattered light reflected from the object in the form of an object beam is constructively interfered with a reference beam or wave (e.g., via a local oscillator) to form a hologram. The constructive interference of the object and reference beams allows for both magnitude and phase information about signals reflected from the object to be measured and recorded. Reconstruction of an image of the object occurs through post-processing of the hologram, in effect creating a digital lens, as opposed to using an actual lens, as found in conventional imaging systems. This digital lens allows for images of objects at all distances to be reconstructed from a single hologram.

FIG. 1A illustrates an imaging system that does not utilize holographic imaging techniques. In the example of FIG. 1A, an object 100 (e.g., a quarter) is viewed through a lens 110, which focuses an image of the object onto an array 120 at a focal length f. The distance f represents the specific distance for this particular lens system at which the object 100 is brought into focus at the array 120 to result in image 130.

Figure 1B:
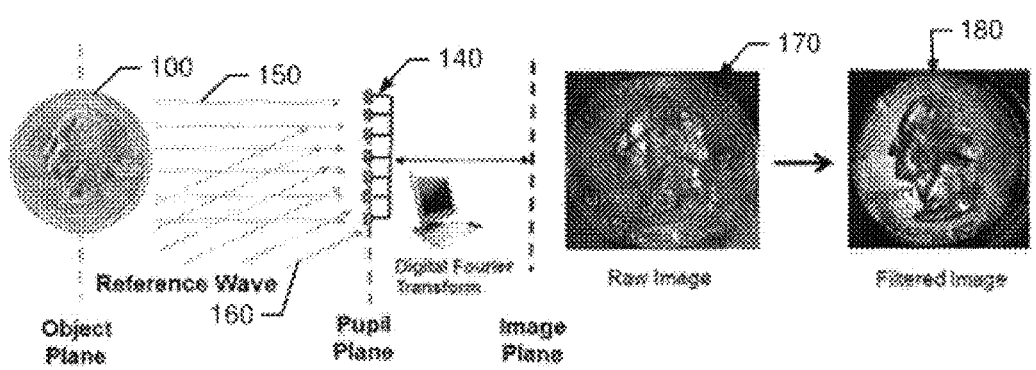
FIG. 1B illustrates a conceptual diagram showing one example of a holographic imaging system.

FIG. 1B illustrates an imaging system that utilizes a holographic imaging technique in which the object 100 is imaged at an array 140 based on scattered light 150 reflected from the object 100. The scattered light 150 may be constructively interfered with by reference wave 160. A raw image 170, and then a filtered image 180, may be generated using image processing techniques such as, for example, discrete Fourier transform (DFT) of data associated with the image collected at the array 140. As can be appreciated from FIG. 1B, holographic imaging is a coherent optics-based approach that may optically filter diffuse photons to achieve a diffraction-limited resolution image in highly scattering mediums. The resolution and field-of-view (FOV) of the image is dictated by the size of the hologram (imaging array) and the distance to the object.

Some example embodiments may enable the provision of a system capable of employing holographic imaging techniques for detecting neural signatures that can, for example, allow medical imaging applications to be undertaken. Thus, for example, high quality imaging may be achieved without bulky equipment. Brain to computer interface (BCI) technology and other applications may, therefore, be improved by providing practically feasible sensors to be employed for real-time processing of neural signatures.

Example embodiments may allow relatively small sensors to be placed on the head to detect neural signatures through the skin and skull of the head at various depths. Another approach is to place the sensor inside the skull either on the surface of the cortex to image the surface of the neural tissue, or within the neural tissue itself. In this regard, for example, some embodiments may provide a structure that allows data to be gathered for multiple depths within the neural tissue using a relatively small package or form factor. To accomplish generation of data corresponding to multiple depths, example embodiments may employ a beam angle separator that allows an object beam to be split into multiple reference beams. Each reference beam may serve as a corresponding different reference wave for generating constructive interference for holographic imaging. Moreover, each reference beam may correspond to image data generated for a respective different depth within the object. As such, using a beam angle separator having any desired number of windows therein may enable a relatively small structure to provide image gathering capability at the same number of depths within the object as the number of windows contained within the beam angle separator.

Figure 2:
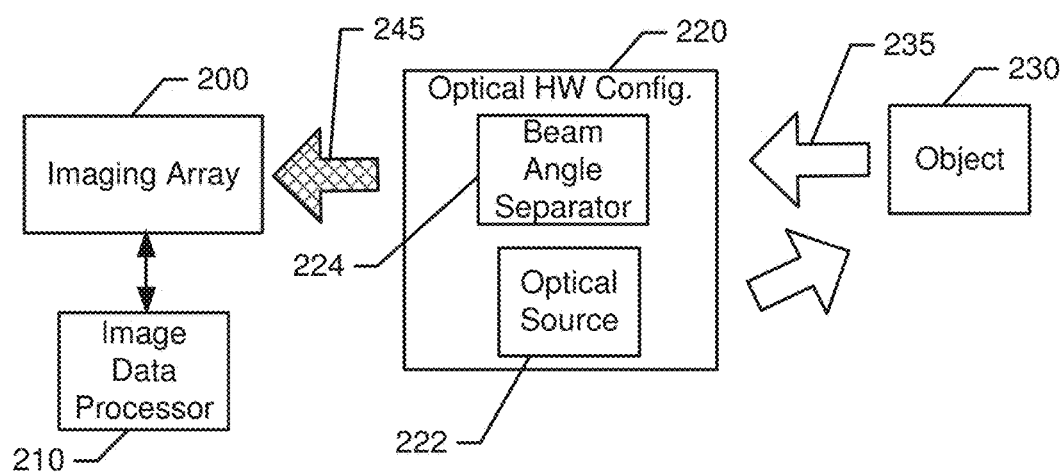
FIG. 2 illustrates a block diagram of a neural signal detection system of an example embodiment.

FIG. 2 illustrates a block diagram of a system for providing detection of neural signatures using holographic imaging according to an example embodiment. As shown in FIG. 2, the system may include an imaging array 200, image data processor 210, and an optical hardware structure or configuration 220. The imaging array 200 may be, for example, a multi-element detector array or a bare focal plane array. Additionally, in some embodiments, the imaging array 200 does not necessarily require that an image be formed on the array. The optical hardware configuration 220 may include an optical source 222 (e.g., a short-coherence length laser) and a beam angle separator 224, which forms the structure for defining different reference beams or waves within the optical hardware configuration 220. While the optical source 222 as shown in FIG. 2 is located within the optical hardware configuration 220, in other embodiments the optical source 222 may reside externally to the optical hardware configuration 220, or externally to the system illustrated in FIG. 2. Moreover, the image data processor 210 may be operably coupled to the imaging array 200, and may be either in proximity to, or remote from, the imaging array 200.

The optical source 222 may illuminate an object 230 (i.e., the object being imaged), resulting in at least one object beam 235 being reflected from the object 230 and directed toward the imaging array 200 through the optical hardware configuration 220. In an embodiment, the object beam 235 may pass through the beam angle separator 224 to generate multiple reference beams (collectively shown as 245). The imaging array 200 may also be configured to receive object beams (not shown) separate from the object beam 235, which are reflected from the object 230 responsive to illumination of the object 230 by the optical source 222, but may not be passed through the beam angle separator 224. In an embodiment, two (or multiple) color holography may be used to illuminate the object 230 with light of two (or multiple) different optical wavelengths. Surface deformation of the object 230 may be measured based on the relative phase difference between the object beams scattered from the object 230, with each object beam corresponding to a different optical wavelength.

The beam angle separator 224 may separate the object beam 235 into at least two reference beams 245 by an amount of angular separation. The reference beams 245 comprise waves that constructively interfere with the object beams to form a hologram. Light from the resulting constructive interference by the reference beams 245 with the object beams may be received by the imaging array 220, and further processed by the image data processor 210 using holographic image processing techniques similar to those described above in reference to FIG. 1B. For example, for two reference beams, two distinct holograms may be generated as superimposed on one another. The two holograms may be separated from each other during the holographic image processing to generate two different images of the object 230.

As described in greater detail below, the beam angle separator 224 may include a plurality of windows, with each window generating a different reference beam 245 from the object beam 235. Each different reference beam 245 may correspond to an image of the object 230 associated with a different depth within the object 230.

In an example embodiment, the object 230 may be neural tissue or other biological matter of a brain or a head (e.g., human, primate, or other animal). The imaging array 200 and the optical hardware configuration 220 may be provided in a sensor that can be worn on the outer surface of the head, or implanted into a portion of the head. The sensor may detect neural signatures or perform other medical imaging tasks on neural tissue or other biological matter in the brain and the head with relatively high accuracy, but also with relatively low structure, size, weight, and/or power requirements. The image data processor 210 may be a part of the sensor, or may be remotely and operably coupled to the sensor.

Figure 3:
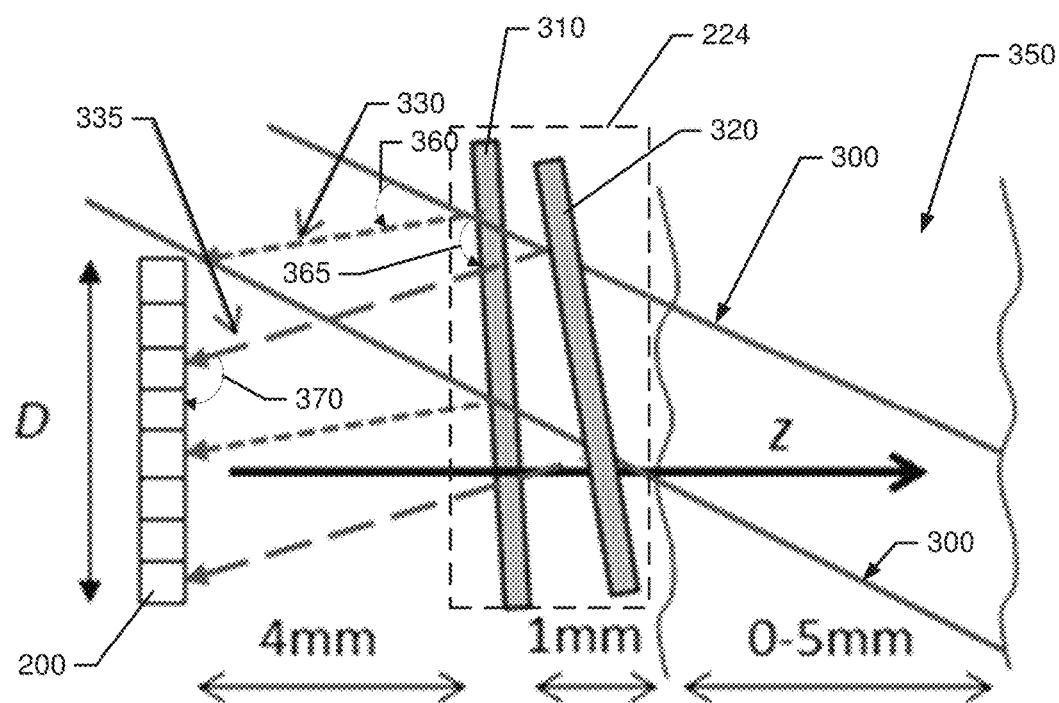
FIG. 3 illustrates a conceptual diagram of some components of the neural signal detection system of an example embodiment within a tissue sample.

FIG. 3 illustrates a conceptual diagram of certain components of the system of FIG. 2, according to an embodiment. Referring to FIG. 3, two instances of object beam 300 are shown passing through a first window 310 and a second window 320 of the beam angle separator 224. It should be appreciated that the lines representing the object beam 300 shown in FIG. 3 may represent portions, or boundaries, of a wider beam. Moreover, the instances of the object beam 300 may exist simultaneously with each other. Furthermore, while two windows are shown in FIG. 3, more than two windows may be included in the beam angle separator 224. Each of the first and second windows 310 and 320 may have substantially the same index of refraction, but each tilt at a different angle relative to the plane in which the imaging array 200 lies. Thus, the first window 310 may tilt at a first angle (e.g., a small angle of less than about five degrees) relative to the imaging array 200, and the second window may tilt at a different, second angle (e.g., less than about ten degrees) relative to the imaging array 200. A first reference beam 330 and a second reference beam 335 may be generated from the first and second windows 310 and 320, respectively, by refraction of the object beam 300 passing through the first and second windows 310 and 320, respectively. The windows in the beam angle separator 224, including the first and second windows 310 and 320, may include relatively thin sheets or panes of glass, plastic, or other translucent materials having, for example, an index of refraction that may be selected or otherwise pre-determined. Furthermore, while the first and second windows 310 and 320 are illustrated as rectangles in FIG. 3, they may be of any suitable shape or size, and of any suitable index of refraction.

In an embodiment, a single object beam 300 may be refracted by the first window 310 and the second window 320, respectively, to form the first reference beam 330 and the second reference beam 335, respectively. As shown in FIG. 3, the first reference beam 330 may refract at a first reference angle 360 relative to the object beam 300 incident on the first window 310, and the second reference beam 335 may refract at a second reference angle 365 relative to the object beam 300 incident on the second window 320. In this example, the second reference angle 365 corresponding to the second reference beam 335 may be larger than the first reference angle 360 corresponding to the first reference beam 330. In other words, the second reference beam 335 has a larger angular separation relative to the object beam 300, and therefore a larger incident angle 370 with respect to the imaging array 200, than the first reference beam 330.

This is due at least in part to the larger tilt angle of the second window 320 relative to the plane of the imaging array 200 than the tilt angle of the first window 310 relative to the plane of the imaging array 200. The difference between the first and second reference angles 360 and 365 may result in different incident angles of the first and second reference beams 330 and 335, respectively, on the imaging array 200. The different incident angles on the imaging array 200 may also be due at least in part to the windows being spaced apart from the imaging array 200 at different distances. The different incident angles on the imaging array 200 correspond to images at different depths in the object 350, so that data generated from the imaging array 200 for the first reference beam 330 correlates to an image of the object 350 at a first depth within the object 350, and data generated from the imaging array 200 for the second reference beam 335 correlates to an image of the object 350 at a different, second depth within the object 350.

Two windows, as provided in the example of FIG. 3, results in the resolution of two specific range bins that can each be brought into focus through post-processing to provide corresponding depth-specific image data in substantially real time. By providing a plurality of windows in the beam angle separator 224, and defining angular separations between the respective reference beam and the object beam for each corresponding window, a three dimensional, fully registered, real-time image may be generated.

In the example of FIG. 3, the object 350 being imaged may be neural tissue or other biological matter that is at a certain depth within the head of an individual. In this example, the first and second window 310 and 320 may be disposed approximately 1 mm (average) apart from each other in order to allow the different tilt angles to be formed therebetween. The thickness of the beam angle separator 224 may be a function of the number of windows contained therein. The higher the number of windows (and therefore the higher the number of depths within the object 350 at which different image data can be generated), the thicker the beam angle separator 224 may be. In this example, the imaging array 200 may be disposed approximately 4 mm away from the beam angle separator 224 in order to generate data at depths ranging from zero to 5 mm into the object 350. While other depths and distances may be employed in other examples, the example of FIG. 3 illustrates that sub-millimeter volumetric spatial resolution is achievable in a sensor that can act as an electrode to monitor brain activity.

Data associated with performing holographic image processing techniques for each respective reference beam may be distinctly processed by the image data processor 210. Thus, for example, separate range bins may be defined for the data associated with each respective reference beam.

Figure 4:
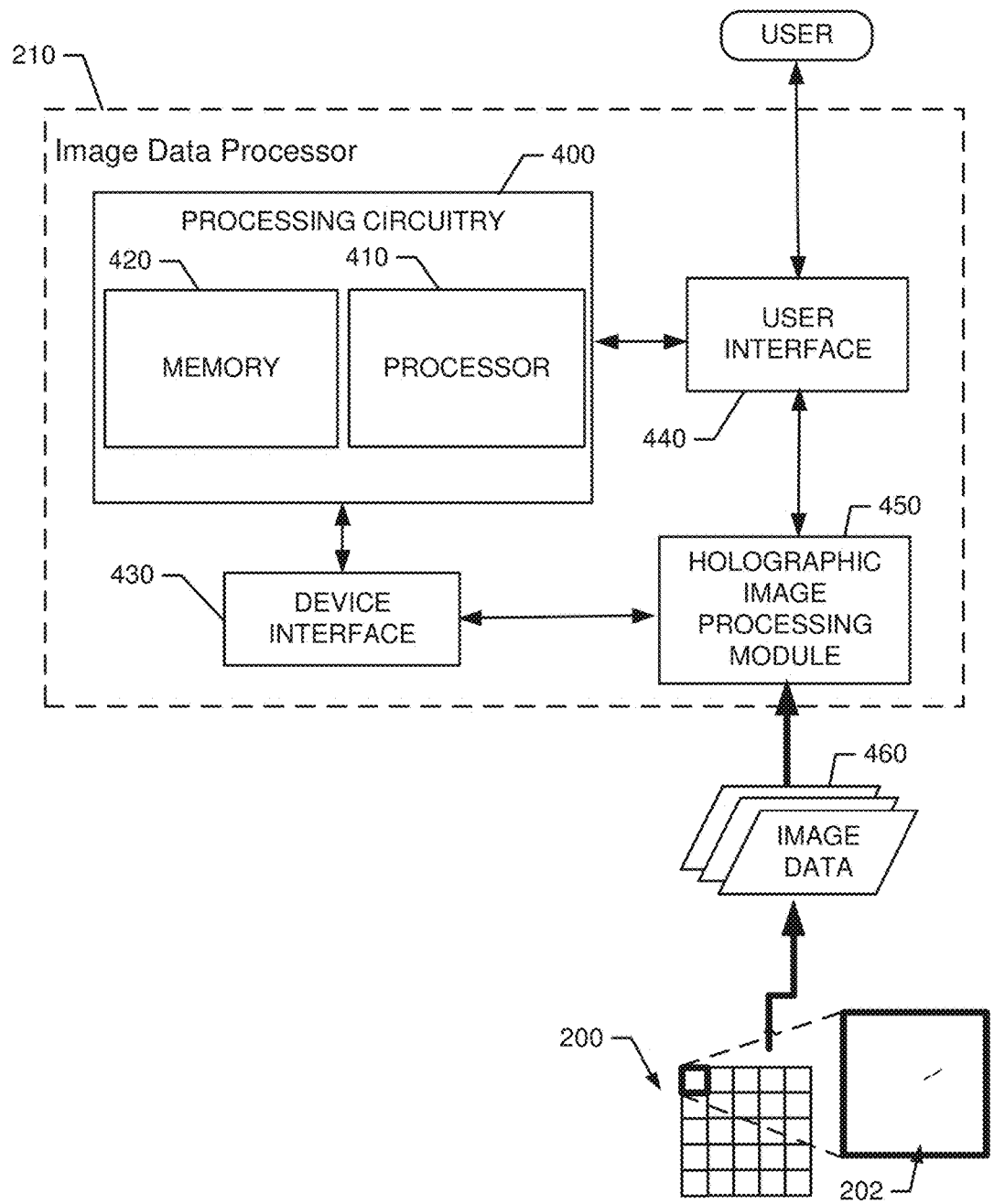
FIG. 4 illustrates a block diagram of an image data processor according to an example embodiment.

FIG. 4 illustrates a block diagram of some components of the system of FIG. 2 in greater detail in accordance with an example embodiment. Referring now to FIG. 4, the image data processor 210 may include or otherwise be in communication with processing circuitry 400 that is configurable to perform actions in accordance with example embodiments described herein. As such, for example, at least some of the functions attributable to the image data processor 210 may be carried out by or otherwise instructed by the processing circuitry 400. The processing circuitry 400 may therefore provide the hardware for hosting software to configure the system for analysis techniques consistent with example embodiments. Detection of neural signatures and corresponding imaging and/or functions driven based on such signatures may then be accomplished using the processing circuitry 400.

The processing circuitry 400 may be configured to perform data processing, control function execution and/or other processing and management services according to an example embodiment of the present invention. In some embodiments, the processing circuitry 400 may be embodied as a chip or chip set. In other words, the processing circuitry 400 may comprise one or more physical packages (e.g., chips) including materials, components and/or wires on a structural assembly (e.g., a baseboard).

In an example embodiment, the processing circuitry 400 may include one or more instances of a processor 410 and memory 420 that may be in communication with or otherwise control a device interface 430 and, in some cases, a user interface 440. As such, the processing circuitry 400 may be embodied as one or more instances of a circuit chip (e.g., an integrated circuit chip) configured (e.g., with hardware, software or a combination of hardware and software) to perform operations described herein.

The user interface 440 (if implemented) may be in communication with the processing circuitry 400 to receive an indication of a user input at the user interface 440 and/or to provide an audible, visual, mechanical or other output to the user. As such, the user interface 440 may include, for example, a display, printer, one or more buttons or keys (e.g., function buttons), and/or other input/output mechanisms (e.g., keyboard, touch screen, mouse, microphone, speakers, cursor, joystick, lights and/or the like). The user interface 440 may display information indicating a neural signature or certain characteristics of a data set (e.g., including images or results of analyzing images) being processed by the image data processor 210. The neural signature or characteristics of the data set may then be processed and information associated therewith may be presented on a display of the user interface 440 based on instructions executed by the processing circuitry 400 for the analysis of the data according to prescribed methodologies and/or algorithms. Moreover, in some cases, the user interface 440 may include options for selection of one or more reports or displays to be generated based on the analysis of a given data set.

The device interface 430 may include one or more interface mechanisms for enabling communication with other external devices (e.g., output devices, input devices and/or the like) or internal functional components of the detection system. In some cases, the device interface 430 may be any means such as a device or circuitry embodied in either hardware, or a combination of hardware and software that is configured to receive and/or transmit data from/to devices in communication with the processing circuitry 400.

In an exemplary embodiment, the memory 420 may include one or more non-transitory memory devices such as, for example, volatile and/or non-volatile memory that may be either fixed or removable. The memory 420 may be configured to store information, data, applications, instructions or the like for enabling the image data processor 210 to carry out various functions in accordance with example embodiments of the present invention. For example, the memory 420 could be configured to buffer input data for processing by the processor 410. Additionally or alternatively, the memory 420 could be configured to store instructions for execution by the processor 410. As yet another alternative or additional feature, the memory 420 may include one or more databases that may store a variety of data sets indicative of patterns that are configured to trigger specific responses or algorithms, image data processing techniques, processing algorithms and/or the like to be employed for the execution of example embodiments. Among the contents of the memory 420, applications may be stored for execution by the processor 410 in order to carry out the functionality associated with each respective application. In some cases, the applications may include directions for control of the image data processor 210 to process images received from the imaging array 200. In particular, in some cases, the applications may include instructions for directing operation of a holographic image processing module 450 relative to sets of image data 460 that each correlate to data associated with a corresponding depth or depth of focus (DOF). In some cases, the applications may further include directions for generating an output as one or more reports, medical imaging displays or other outputs of data or analytical work product associated with analysis of the image data 460 as described herein.

The processor 410 may be embodied in a number of different ways. For example, the processor 410 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 410 may be configured to execute instructions stored in the memory 420 or otherwise accessible to the processor 410. As such, whether configured by hardware or by a combination of hardware and software, the processor 410 may represent an entity (e.g., physically embodied in circuitry—in the form of processing circuitry 400) capable of performing operations according to embodiments of the present invention while configured accordingly. Thus, for example, when the processor 410 is embodied as an ASIC, FPGA or the like, the processor 410 may be specifically configured hardware for conducting the operations described herein. Alternatively, as another example, when the processor 410 is embodied as an executor of software instructions, the instructions may specifically configure the processor 410 to perform the operations described herein.

In an example embodiment, the processor 410 (or the processing circuitry 400) may be embodied as, include or otherwise control the image data processor 210. As such, in some embodiments, the processor 410 (or the processing circuitry 400) may be said to cause each of the operations described in connection with the image data processor 210 and/or the holographic image processing module 450 by directing the image data processor 210 and/or the holographic image processing module 450 to undertake the corresponding functionalities responsive to execution of instructions or algorithms configuring the processor 410 (or processing circuitry 400) accordingly.

The holographic image processing module 450 may be configured to process image data 460 received from the imaging array 200 separately for each discrete reference wave, which is correlated with a corresponding depth. Thus, range data may be separately processed (in parallel or series) in order to generate respective different data sets corresponding to each respective depth. The holographic image processing techniques employed may be similar to those discussed above in reference to FIG. 1B. However, additional processing may also be included. For example, in some cases, holographic images may be degraded due to the presence of speckle. Speckle may include granular noise that inherently exists in and degrades the quality of various imaging techniques. Speckle may be found for all coherent imaging modalities such as radar and synthetic aperture radar. One approach to mitigate speckle is through the use of "multi-look" processing, whereby time-sequenced holographic images may be acquired, generated, or obtained using holographic imaging techniques and then registered and averaged to reduce speckle noise. The speckle tends to move due to relative motion between the object and image plane, so for a moving platform or dynamic target, one gets a sqrt(N) improvement in image contrast. In general, acquisition of more than four sequential images may begin to show noticeable image quality improvement. By averaging four or more images, the frame rate or data acquisition rate of the system is effectively decreased, which can impact image performance/resolution for dynamic events.

A digital holographic system may otherwise not be able to control beam diameter or detector size in order to mitigate speckle. Accordingly, in some example embodiments, a technique may be employed to divide the imaging array 200 into multiple sub-arrays 202 to reduce speckle noise. The use of sub-arrays 202 effectively creates a multi-look situation that allows multiple speckle realizations to be averaged to minimize image degradation. However, the multi-look situation is actually created from a single look using the sub-arrays 202. By employing sub-arrays 202, image registration may be relatively straightforward since such registration is only based on the relative location of the different sub-arrays. In addition, division into sub-arrays also allows for the effective frame rate to match the fastest frame rate of the camera. The holographic image processing module 450 may therefore be configured to further process image data 460 received from a plurality of overlapping or non-overlapping sub-arrays 202. Combining multiple sub-arrays 202 also improves the signal-to-noise ratio of each image, which permits imaging of objects at either greater distances or through greater amounts of scatter such as found in biologic samples.

Depth resolution for a single wavelength holographic imaging system is determined by the DOF of the system. DOF is a function of both the array size and the object range and can vary from millimeters to meters depending on imaging conditions. Leveraging the DOF for a highly scattering medium is ineffective because of the "noise" generated by the scattered light both before and after the range of interest. To address this issue, some example embodiments may employ a short coherence length laser as the optical source 222. Similar to optical coherence tomography (OCT), the range resolution may then be determined by the coherence length of the optical source 222. However, OCT is limited to a penetration depth in biologic samples of less than 2 mm due to a desire to provide the highest depth resolution (~10 microns). Brain computer interface (BCI) applications do not necessarily require that level of resolution, so a high-power moderate coherence length laser (~1 mm) may be employed to enable much greater depth penetration (e.g., greater than ten millimeters). These depths are relevant for both animal and human models. Combining holographic imaging with the short coherence length laser may enable resolution of specific range bins that can each be brought into focus through post-processing by the holographic image processing module 450 to provide a full 3D, fully registered, real-time, image.

In some cases, the short-coherence length laser may facilitate simultaneous acquisition of multiple range bins. To separate the reconstructed images, multiple reference beams may be used, each with a slightly different reference (or incident) angle as discussed above in reference to FIGS. 2 and 3. The reference (or incident) angle of the reference beam effectively places a spatial carrier on the hologram, which then can be used to spatially separate the reconstructed images and segregate sets of image data 460 by depth. The structure of the beam angle separator may therefore facilitate separation of separate reference beams at a single wavelength with a short coherence length.

The short-coherence length laser with multiple reference beams at different distances can be implemented into a small package ideally suited for sensors embedded into a person or animal. As shown in FIG. 3, the use of multiple windows, each at a slightly different tilt angle permits the use of a single laser and single imaging array, which will dramatically reduce size, weight, and power of the total system. The post-processing performed by the holographic image processing module 450 thereafter allows the separate reference beams to be used for holographic image analysis to determine image data at respective different depths with sub-millimeter spatial resolution.

Figure 5:
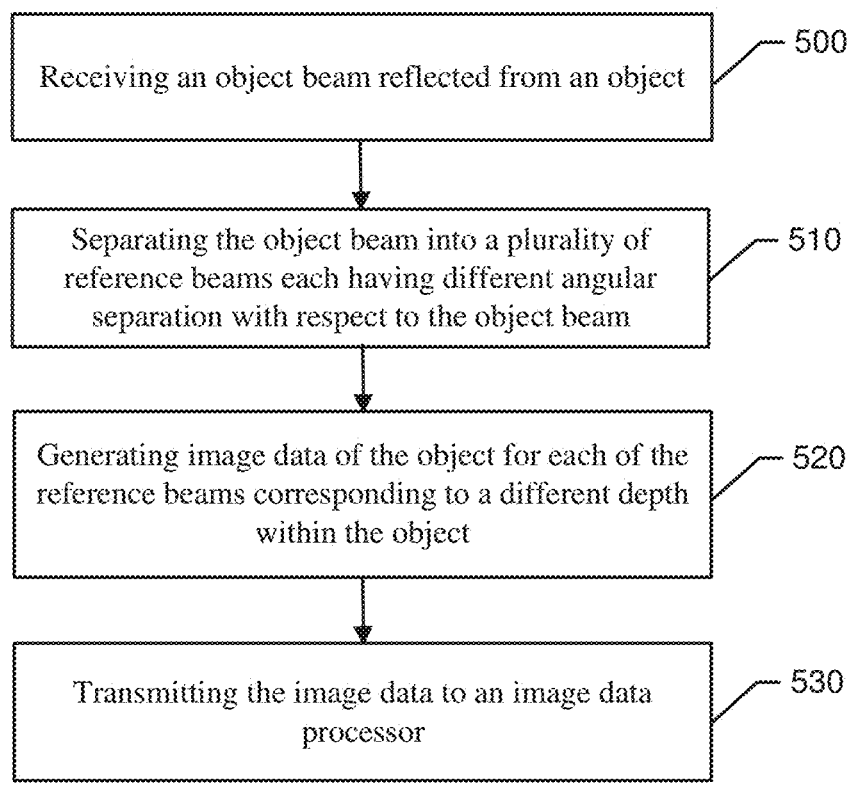
FIG. 5 shows a block diagram of a method according to an example embodiment.

FIG. 5 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a sensor, electrode or processing circuitry associated therewith and executed by a processor in the sensor, electrode or processing circuitry associated therewith. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of determining a neural signature using a centimeter or smaller beam according to one embodiment of the invention is shown in FIG. 5. The method of FIG. 5 may entirely, or at least in part, be executed automatically (e.g., without operator interaction to initiate each step or the series of steps) by processing circuitry. The method may include receiving an object beam reflected from an object at operation 500. The method may further include separating the object beam into a plurality of reference beams each having different angular separation with respect to the object beam at operation 510. The method may further include generating image data of the object for each of the reference beams corresponding to a different depth within the object at operation 520, and transmitting the image data to an image data processor at operation 530.

In some embodiments, additional optional operations may be included or the operations described above may be modified or augmented. Each of the additional operations, modification or augmentations may be practiced in combination with the operations above and/or in combination with each other. Thus, some, all or none of the additional operations, modification or augmentations may be utilized in some embodiments. In an example embodiment, separating the object beam may include refracting the object beam into the plurality of reference beams with a corresponding plurality of windows in a beam angle separator, each of the windows defining a respective different one of the reference beams. In some cases, generating the image data may include generating image data corresponding to different depths for each respective one of the windows. In an example embodiment, refracting the object beam into the plurality of reference beams with the corresponding plurality of windows may include refracting the object beam into the reference beams such that each reference beam corresponds to a different one of the windows. In such an example, each of the windows may have a same index of refraction. In an example embodiment, refracting the object beam into the plurality of reference beams with the corresponding plurality of windows may include refracting the object beam into the reference beams such that each of the windows is disposed or tilted at a different angle relative to a plane of the imaging array. Additionally or alternatively, a plurality of sub-arrays may be defined in the imaging array. In some cases, four sub-arrays may be defined and the sub-arrays sequentially acquire at least four images. In such an example, the method may further include averaging the at least four images at the image data processor. In an example embodiment, the method may further include providing an optical source to generate the object beam. The optical source may be a moderate or short coherence length laser. In some examples, the method may further include providing the imaging array and beam angle separator in a sensor. In such an example, the object may be a brain and the different depths may be different depths measured in the brain via the sensor implanted in a head of an individual or worn on the head of the individual.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A neural imaging system comprising:
an imaging array;
an image data processor operably coupled to the imaging array to process image data received from the imaging array; and
a beam angle separator disposed between the imaging array and an object being imaged,
wherein the beam angle separator is configured to separate an object beam reflected from the object being imaged into a plurality of reference beams each having different angular separation with respect to the object beam,
wherein the image data processor is configured to generate image data of the object for each of the reference beams, the image data for each of the reference beams corresponding to a different depth within the object, and
wherein the beam angle separator comprises a plurality of windows, each of the windows refracting the object beam into a respective different one of the reference beams.

2. The neural imaging system of claim 1, wherein a number of the plurality of windows corresponds to a number of different depths within the object at which image data is generated.

3. The neural imaging system of claim 1, wherein each of the windows has a substantially same index of refraction.

4. The neural imaging system of claim 1, wherein each of the windows is tilted at a different angle relative to a plane of the imaging array.

5. The neural imaging system of claim 1, wherein the imaging array comprises a plurality of sub-arrays.

6. The neural imaging system of claim 5, wherein the imaging array comprises at least four sub-arrays configured to sequentially acquire at least four images of the object.

7. The neural imaging system of claim 1, further comprising an optical source, wherein the object beam is generated responsive to the optical source illuminating the object.

8. The neural imaging system of claim 7, wherein the optical source comprises a moderate or short coherence length laser.

9. The neural imaging system of claim 1, wherein the object comprises neural tissue and the different depths comprise different depths within the neural tissue.

10. A method comprising:
receiving an object beam reflected from an object;
separating the object beam into a plurality of reference beams each having different angular separation with respect to the object beam, wherein separating the object beam comprises refracting the object beam into the plurality of reference beams using a corresponding plurality of windows, each of the windows defining a respective different one of the reference beams;

generating image data of the object for each of the reference beams corresponding to a different depth within the object; and transmitting the image data to an image data processor.

11. The method of claim 10, wherein generating the image data comprises generating image data corresponding to a different depth within the object for each respective one of the windows.

12. The method of claim 10, further comprising receiving, by an imaging array, light resulting from constructive interference of the reference beams with a plurality of object beams, separate from the object beam, that are reflected from the object.

13. The method of claim 10, wherein image data for each reference beam is generated based at least on an incident angle of the respective reference beam on an imaging array.

14. A brain computer interface sensor, comprising:
an imaging array configured to be operably coupled to an image data processor to process image data received from the imaging array; and
a beam angle separator disposed between the imaging array and neural tissue being imaged,
wherein the beam angle separator is configured to separate an object beam reflected from the neural tissue being imaged into a plurality of reference beams each having different angular separation with respect to the object beam,
wherein the beam angle separator comprises a plurality of windows, each of the windows refracting the object beam into a respective different one of the reference beams.

15. The brain computer interface sensor of claim 14, wherein each of the reference beams corresponds to an image at a different depth within the neural tissue.

16. The brain computer interface sensor of claim 14, wherein each of the windows has a substantially same index of refraction.

17. The brain computer interface sensor of claim 14, wherein each of the windows is tilted at a different angle relative to a plane of the imaging array.

18. The neural imaging system of claim 1, wherein each reference beam is received by the imaging array at a respective incident angle relative to a plane of the imaging array due to each reference beam having different angular separation, and
wherein the image data processor is configured to generate the image data of the object for each of the reference beams based on the respective incident angles.

19. The method of claim 10, further comprising receiving, at an imaging array, each reference beam at a respective incident angle relative to a plane of the imaging array due to each reference beam having different angular separation.

20. The brain computer interface sensor of claim 14, wherein each reference beam is formed to be received by the imaging array at a respective incident angle relative to a plane of the imaging array due to each reference beam having different angular separation, and wherein the reference beams are distinguishable based on the respective incident angle for each of the reference beams.

* * * * *